US00RE44763E

(19) United States
(12) Reissued Patent
Dinh et al.

(10) Patent Number: US RE44,763 E
(45) Date of Reissued Patent: Feb. 11, 2014

(54) EXPANDABLE UNIT CELL AND INTRALUMINAL STENT

(75) Inventors: Linh A. Dinh, Santa Clara, CA (US); Loc X. Phan, San Jose, CA (US); Robert Eury, Cupertino, CA (US); Irina Pomerantseva, Wakefield, MA (US); Michael Froix, Mountain View, CA (US)

(73) Assignee: Boston Scientific Scimed, Inc., Maple Grove, MN (US)

(21) Appl. No.: 10/061,458

(22) Filed: Feb. 1, 2002
(Under 37 CFR 1.47)

Related U.S. Patent Documents

Reissue of:
(64) Patent No.: 6,019,789
Issued: Feb. 1, 2000
Appl. No.: 09/053,887
Filed: Apr. 1, 1998

(51) Int. Cl.
*A61F 2/06* (2013.01)

(52) U.S. Cl.
USPC ..... 623/1.15

(58) Field of Classification Search
USPC ..... 623/1.15, 1.1–1.2, 1.11, 1.12, 1.16, 623/11.11, 12.11
See application file for complete search history.

(56) References Cited

U.S. PATENT DOCUMENTS

| | | | | |
|---|---|---|---|---|
| 4,722,655 | A | 2/1988 | Bonerb | 414/288 |
| 4,733,665 | A | 3/1988 | Palmaz | 128/343 |
| 4,739,762 | A * | 4/1988 | Palmaz | 623/1.11 |
| 5,195,984 | A * | 3/1993 | Schatz | 623/1.2 |
| 5,342,348 | A * | 8/1994 | Kaplan | 604/891.1 |
| 5,354,309 | A * | 10/1994 | Schnepp-Pesch et al. | 606/198 |
| 5,394,390 | A | 2/1995 | Stauffer et al. | 370/17 |
| 5,395,390 | A * | 3/1995 | Simon et al. | 623/1.18 |
| 5,514,154 | A * | 5/1996 | Lau et al. | 623/1.15 |
| 5,568,295 | A | 10/1996 | Nakamura et al. | 359/75 |
| 5,569,295 | A * | 10/1996 | Lam | 606/198 |
| 5,591,197 | A * | 1/1997 | Orth et al. | 623/1.16 |
| 5,593,442 | A * | 1/1997 | Klein | 623/23.64 |
| 5,601,593 | A * | 2/1997 | Freitag | 623/1.19 |
| 5,603,721 | A * | 2/1997 | Lau et al. | 606/195 |
| 5,637,113 | A * | 6/1997 | Tartaglia et al. | 623/1.42 |
| 5,649,952 | A * | 7/1997 | Lam | 623/1.15 |
| 5,674,242 | A * | 10/1997 | Phan et al. | 606/198 |
| 5,674,278 | A * | 10/1997 | Boneau | 623/1.15 |
| 5,697,971 | A | 12/1997 | Fischell | 623/1 |
| 5,755,776 | A * | 5/1998 | Al-Saadon | 623/1.15 |
| 6,183,506 | B1 | 2/2001 | Penn et al. | 623/1.15 |
| 6,231,598 | B1 * | 5/2001 | Berry et al. | 623/1.15 |
| 6,758,860 | B1 * | 7/2004 | Penn et al. | 623/1.16 |
| 2001/0016770 | A1 * | 8/2001 | Allen et al. | 623/1.15 |

FOREIGN PATENT DOCUMENTS

| | | | |
|---|---|---|---|
| DE | 297 08 879 | U1 | 9/1997 |
| EP | 0 806 190 | A1 | 11/1997 |
| WO | 97/32543 | A1 | 9/1997 |
| WO | 98/05270 | A1 | 2/1998 |

* cited by examiner

*Primary Examiner* — Alvin J. Stewart
(74) *Attorney, Agent, or Firm* — Vidas, Arrett & Steinkraus

(57) ABSTRACT

A unit cell for use in a medical device, such as a stent, is disclosed along with a description of a stent formed from a plurality of unit cells and for use in the treatment of restenosis or other vascular narrowing. The unit cell is designed and configured for uniform radial expansion with minimal axial shortening and recoil, and is selectively variable in flexibility and expendability.

33 Claims, 14 Drawing Sheets

EXPANDABLE UNIT CELL AND INTRALUMINAL STENT

Matter enclosed in heavy brackets [ ] appears in the original patent but forms no part of this reissue specification; matter printed in italics indicates the additions made by reissue.

FIELD OF THE INVENTION

The present invention relates generally to medical devices, and particularly to a unit cell for use in an expandable endoprosthesis device, more generally called a stent, and to a stent composed of such unit cells.

BACKGROUND OF THE INVENTION

Stents are generally cylindrically shaped devices which are radially expandable for implantation into a body lumen for holding open a segment of a blood vessel or other anatomical lumen. Stents have found a particular use in maintaining vessel patency following angioplasty, e.g., in preventing restenosis of the vessel.

Stents are typically inserted into the damaged vessel by mounting the stent on a balloon catheter and advancing the catheter to the desired location in the patient's body, inflating the balloon to expand the stent and then deflating the balloon and removing the catheter. The stent in its expanded condition in the vessel exerts a radial pressure on the vessel wall at the lesion site, to counter any tendency of the vessel to close.

Although a variety of stents have been proposed, none to date has proven to be entirely satisfactory. For example, one problem with prior art stents has been contraction of the stent along its longitudinal length upon radial expansion of the stent. This can cause problems in correctly placing the stent within the vessel.

Another problem with prior art stents has been the limited range of expandability. Some stents expand only to a limited degree, necessitating fabrication of stents in a range of diameters, increasing cost of manufacture and posing difficulty in selecting the proper stent size for the vessel to be treated.

Another problem area has been a lack of control over the final, expanded diameter of the stent. The expansion of the stents is a function of the particular design or configuration and the spring constant and modulus of elasticity of the material used to manufacture the stent. Many stents because of their design and configuration exhibit recoil after expansion, making secure placement of the stent at the treatment site difficult. Poor contact between the stent and the vessel wall not only allows for some closure of the vessel, but can lead to more serious complications including migration of the stent away from the desired location. This problem is not readily solved by attempting to compensate for recoil by selecting an oversized stent, since improper selection may result in a stent which exerts to much force of the vessel, leading to an increase in the possibility of vessel injury, such as dissection or intimal hyperplasia.

Another problem area has been in meeting the requirement that the stent be capable of maintaining the radial rigidity and strength needed to hold open a vessel while at the same time maintaining the longitudinal flexibility of the stent to facilitate its delivery. Placement of stents often involves advancing the stent-catheter assembly through tortuous vascular paths to the treatment site.

It is also important that the stent have a low-profile for intra-luminal delivery and that it be suited for deployment by a delivery system that is reliable and easy to operate.

SUMMARY OF THE INVENTION

It is one object of the present invention to provide a stent which substantially overcomes the limitations of the prior art.

It is another object of the present invention to provide a stunt having a selectively variable radial rigidity and longitudinal flexibility.

It is another object of the present invention to provide a stent which does not exhibit significant recoil after implantation.

It is a further object of the present invention to provide a stunt having the above features and further capable of carrying a polymer member thereon. In one aspect, the invention includes a unit cell for use in a stent adapted to be expanded to conform to the dimensions of a vessel. The unit cell includes:

(i) an elongate connecting bar extending in a direction normal to the direction of stent expansion, (ii) associated with each end of said connecting bar, a first arm and a second arm, each arm being attached to the connecting bar associated end at an inner arm end for pivotal movement away from one another with stunt expansion; the first and second arms having outer arm ends which are moved outwardly, with respect to the connecting bar, with such pivotal movement, and (iii) an expandable looped member connecting the outer arm ends in each pair of first and second arms; the looped member having an axial [extremity which moves axially inwardly, with respect to the associated connecting bar end,] *component length as measured in an axial direction from an axial outward extremity to an axial inward extremity, wherein the axial component length reduces in length* with stunt expansion.

The arms and expandable looped members are constructed and dimensioned so that the [radial] *axial* outward distance traveled by the arms' outer ends in each pair of first and second arms is approximately equal to the [axial inward distance traveled by the associated looped member extremity,] *reduction in length of the axial component length of the associated looped member* as the stent is expanded.

In one embodiment of the unit cell, the first and second arms in each pair are connected to the respective looped members through a shoulder member. The shoulder member can be a U-shaped, N-shaped or W-shaped shoulder member.

In a preferred embodiment, the looped members of the unit cell have an undulating configuration.

In another aspect, the invention includes a stunt adapted to be expanded to conform to the dimensions of a vessel, comprising a plurality of unit cells as described above.

In one embodiment, the stent is composed of a first plurality of unit cells connected to one or more axially adjacent plurality of unit cells by at least one connecting segment extending between two axially adjacent axial extremities. Each plurality of unit cells can include between about 3-500 unit cells.

The stent has an expansion ratio, taken as the diameter of the stent after expansion to the diameter before expansion, of between about 1-10. In various embodiments, the expansion ratio is varied by varying the axial length, taken as the distance between axial extremities in a unit cell, of the unit cells in each plurality of unit cells, or by varying the number of unit cells in each plurality.

In another embodiment of the invention, the stent further includes an outer stent surface on which a polymer stent is carried. The stent and polymer stent are designed for coexpansion in response to an applied force.

*In some embodiments, a stent comprises a plurality of serpentine circumferential bands including first serpentine circumferential bands of a first shape and second serpentine circumferential bands of a second shape different from the first shape. Adjacent serpentine circumferential bands are connected one to the other. Every first serpentine circumferential band is adjacent to a said second serpentine circumferential band and every second serpentine circumferential band is adjacent to a said first serpentine circumferential band. The distal most openings of the stent are at least partially bounded by a said first serpentine circumferential band and at least partially bounded by a said second serpentine circumferential band. The proximal most openings of the stent are at least partially bounded by a said first serpentine circumferential band and at least partially bounded by a said second serpentine circumferential band. At least one opening is not bounded by a said second serpentine circumferential band.*

These and other objects and features of the invention will be more fully appreciated when the following detailed description of the invention is read in conjunction with the accompanying drawings.

DETAILED DESCRIPTION OF THE INVENTION

Figure 1A:
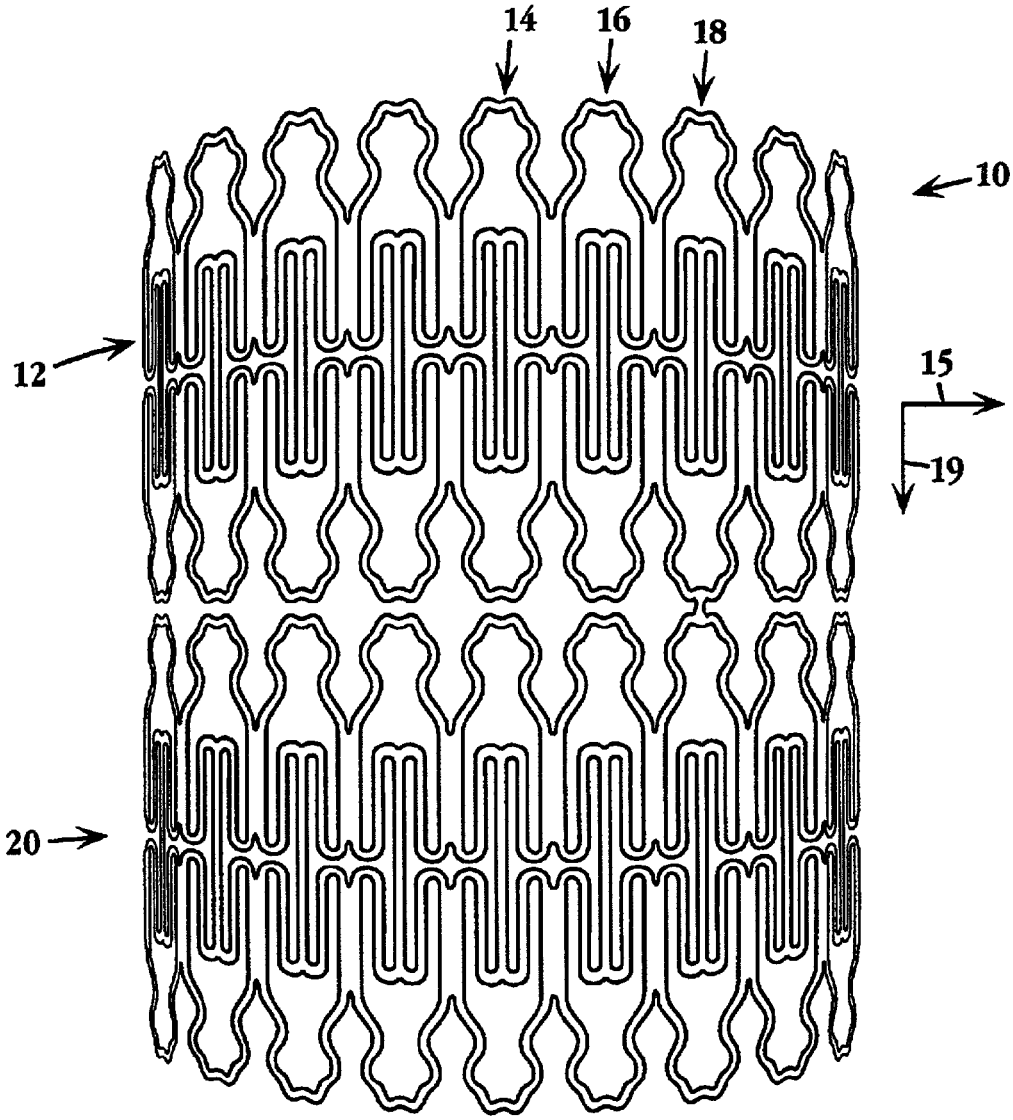
FIGS. 1A-1B are perspective-elevational views of one embodiment of the stent of the present invention, where the stent is shown in its small-diameter, unexpanded condition (FIG. 1A) (the backside of the stent is not shown for clarity) and in its large-diameter, expanded condition (FIG. 1B)

Referring to FIG. 1A, an embodiment of the stent, or endovascular support device, of the present invention is shown. Stent 10 is shown in its unexpanded, small diameter condition for insertion in a vessel. The back side of the cylindrical stent is not shown for clarity purposes. Stent 10 is composed of a plurality 12 of unit cells, such as unit cell 14, which will be described hereinbelow. Unit cell 14 is joined in a radial direction, which is indicated in the figure by arrow 15, to unit cell 16, which is connected to unit cell 18, and so on to form plurality 12. Plurality 12 is connected in an axial direction, that is, in a direction normal to the radial direction of stent expansion, as indicated by arrow 19, to a second plurality of unit cells 20. Stent 10 is illustrated with two plurality of unit cells, where each plurality includes nine unit cells, it will be appreciated that any number of pluralities containing any number of unit cells can be selected, as will be described below, depending on the desired stent expansion ratio and the size or length of the lesion to be treated.

Stent 10 is adapted to be expanded to conform to the dimensions of a vessel. Typically, the stent is mounted on an expandable member of a delivery catheter, for example a balloon, and the catheter-stent assembly is introduced into a body lumen for deployment of the stent at the implantation site by inflation of the balloon and expansion of the stent.

Figure 1B:
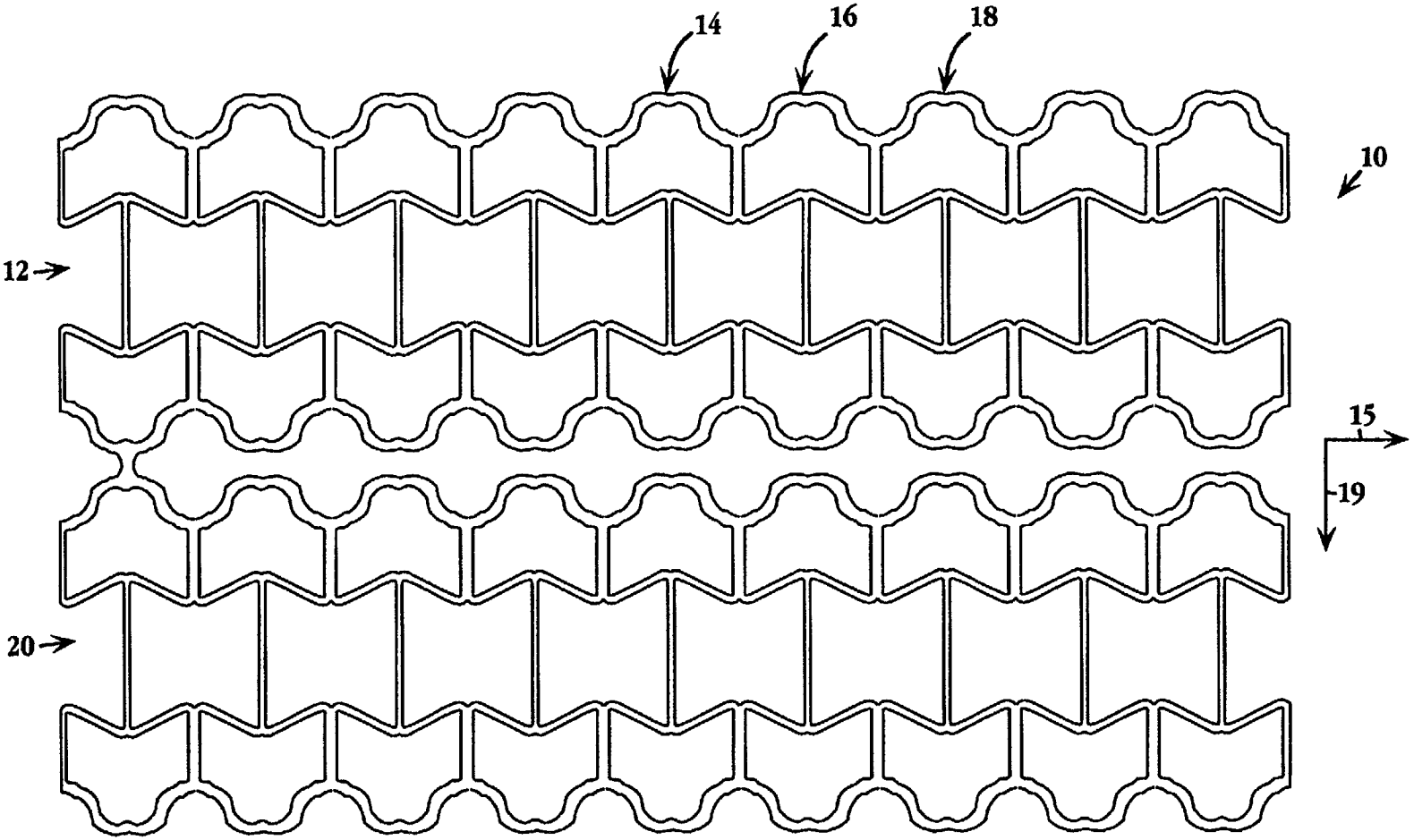

The stent of FIG. 1A in its expanded, larger-diameter form is shown in FIG. 1B. The stent, and more particularly, the unit cells of the stent, are constructed and dimensioned, as will be described below, so that the stent radially expands with limited contraction in the axial direction, e.g., along the length of the stent which is indicated in FIG. 1B by arrow 19. As can be seen in FIG. 1B, the stent has an open reticulated structure allowing for blood perfusion over a substantial portion of the vessel wall against which the stent is biased, to facilitate healing and repair of the damaged vessel.

Figures 2A, 2B:
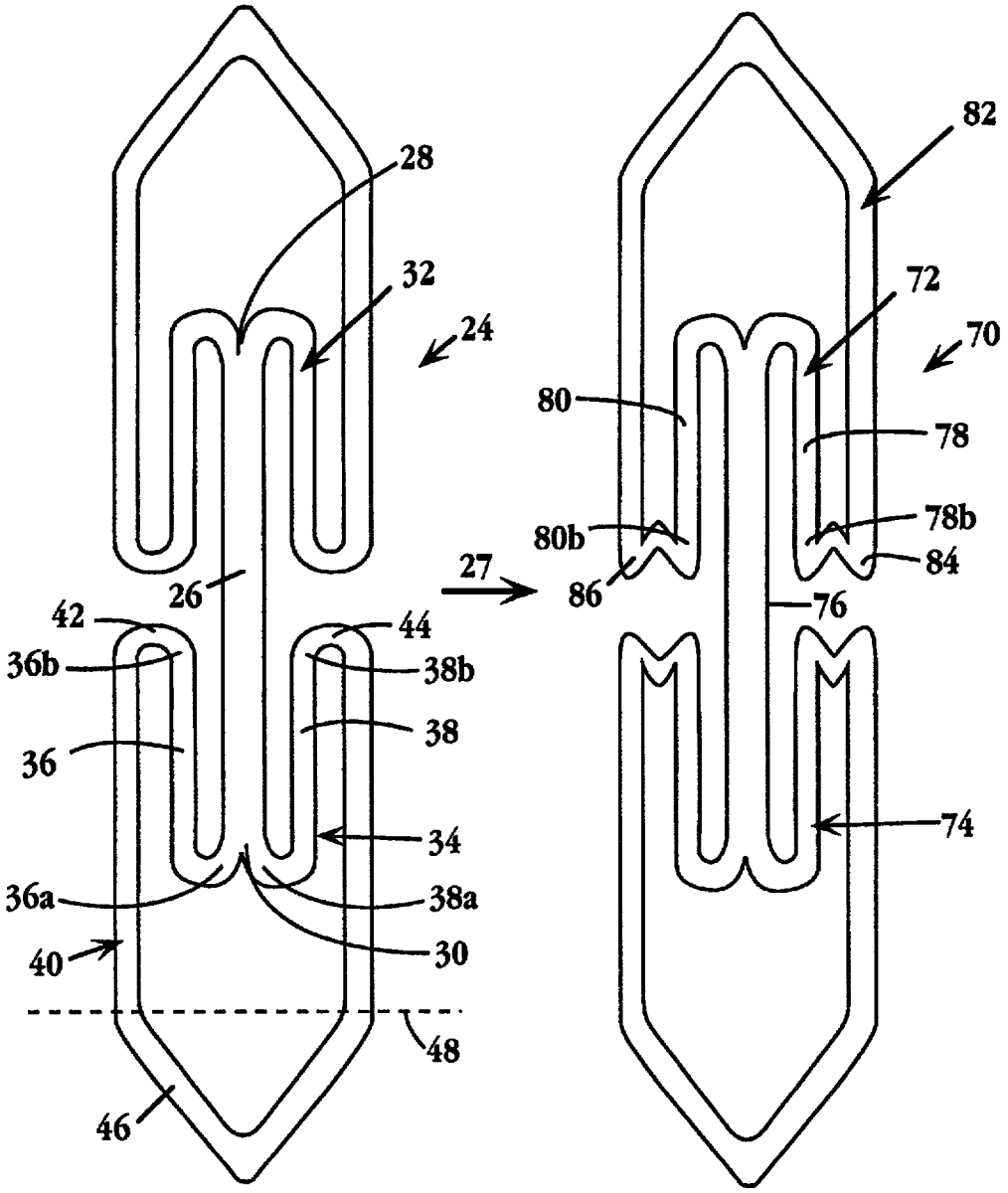
FIGS. 2A-2B are plan views showing the structural detail of a unit cell according to different embodiments of the invention.

The features of the unit cell for use in the stent will be presented through illustration of various embodiments of the unit cell, as shown in FIGS. 2-4. With initial reference to FIG. 2A, a unit cell 24 in its unexpanded, small-diameter condition is shown. The unit cell includes an elongate bar 26, also referred to herein as a connecting bar or an elongate connecting bar, which extends in a direction normal to the direction of stent expansion. The direction of stent expansion is indicated in the figure by arrow 27. Associated with each end 28, 30 of the connecting bar is a pair of arms, which are indicated in the figure as arm pairs 32 on bar end 28 and arm pair 34 on bar end 30. Arm pair 34 includes a first arm 36 and a second arm 38 attached to the associated bar end at inner arm ends 36a, 38a. Arms 36, 38 are attached to the connecting bar for pivotal movement away from one another, as will be described below with reference to FIG. 3.

With continuing reference to FIG. 2A, arms 36, 38 as well as the arms of arm pair 32 at the opposite end of the connecting bar, are attached at an outer arm end, such as ends 36b, 38b, to an expandable looped member, such as member 40. The arm pairs are attached to their respective looped members through U-shaped shoulder members 42, 44 which provide strain relief during expansion of the unit cells of the stent, to offset the radial expansion with axial inward movement of the axial extremity, to limit shortening of the stent. Expandable looped member 40 includes an axial extremity 46, taken as the tip or nose portion of looped member 40, e.g., that portion which is, with respect to the drawing, 'below' dashed line 48.

As noted above, the stent arm pairs are attached to each end of the connecting bar for pivotal movement away from the opposing arm in each pair, and away from the connecting bar, for stent expansion. The outer arm ends of each arm pair move in an outward direction, away from the connecting bar and travel along a path that has a radial and an axial component. The distance the outer arm ends travel in the axial outward direction, that is in the axial direction away from the connecting bar, is approximately equal to the [axial inward distance traveled by the looped member extremity] *reduction in length of the axial component length of the associated looped member as measured in an axial direction from an axial outward extremity to an axial inward extremity of the associated*

*looped member*. This feature of the invention is illustrated more fully below with respect to FIGS. 3A-3B.

*The arms and expandable looped members may also be described as being constructed and dimensioned so that the distance as measured in the axial direction between the axial outward extremities of the opposed expandable looped members of a unit cell is substantially equal before and after stent expansion.*

It will be appreciated that the U-shaped shoulder member of FIG. 2A can have a variety of configurations, such as an N-shape or a W-shape as illustrated in FIG. 2B. In FIG. 2B, stent 70 includes arm pairs 72, 74 connected to elongate bar 76. The first arm 78 and the second arm 80 of arm pair 72 are connected to an expandable looped member 82 at outer arm ends 78b, 80b, through W-shaped shoulder members 84, 86.

Figure 3A:
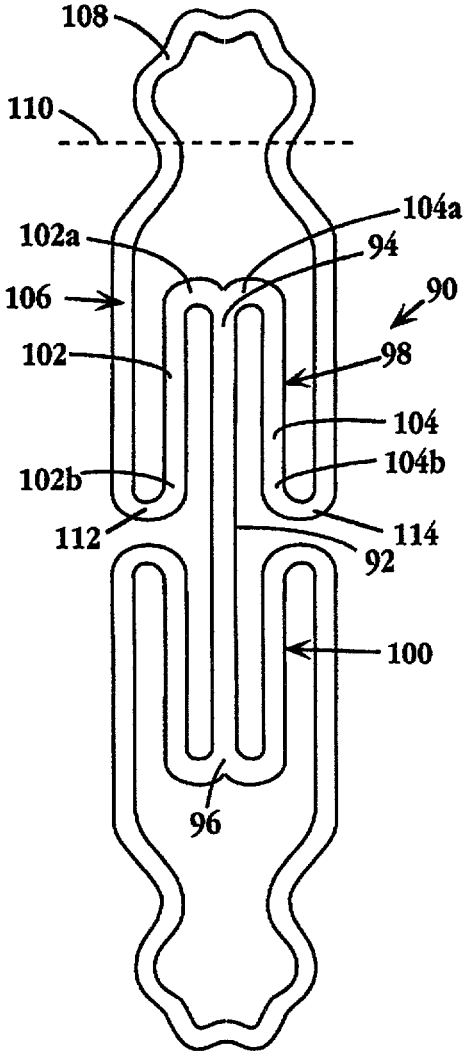
FIGS. 3A-3B are plan views showing the unit cell of the stent of FIG. 1, where the unit cell is shown in its unexpanded condition (FIG. 3A) and in its expanded condition (FIG. 3B)
Figure 3B:
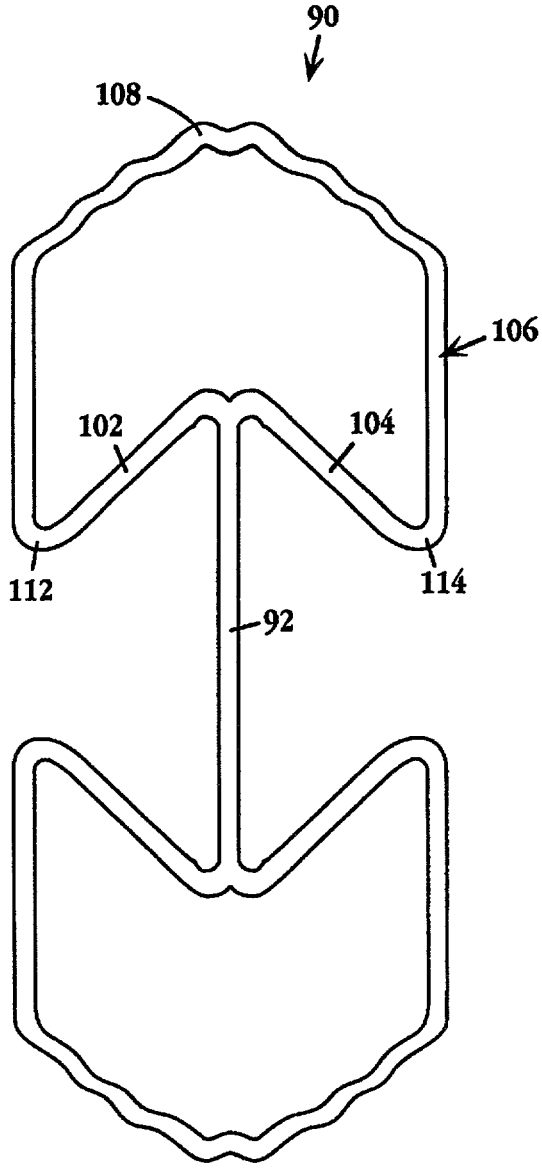

Turning now to FIGS. 3A-3B, a preferred embodiment of the unit cell of the invention is shown, the illustrated unit cell corresponding to the unit cell of the stent shown in FIGS. 1A-1B. Unit cell 90 is shown in FIG. 3A in its small-diameter, unexpanded condition and includes a connecting bar 92. 30 Associated with each end 94, 96 of the connecting bar is a pair of arms 98, 100. Each pair of arms includes a first arm and a second arm, such as arms 102, 104 of arm pair 98. Arms 102, 104 are joined to bar end 94 at inner arm ends 102a, 104a for pivotal movement away from one another with stent expansion. The first and second arms in each pair of arms 98, 100 are joined at an outer arm end, such as ends 102b, 104b of arms 102, 104 respectively, to an expandable looped member, such as member 106, which include an axial extremity, such as extremity 108, taken as the nose portion 'above' (with respect to the drawing) dashed line 110. The first and second arms are joined to the looped member through shoulder members 112, 114, which, in this embodiment, are U-shaped members.

In the embodiment shown in FIG. 3A, the axial extremity in each of the expandable looped members has an undulating or wavy configuration. The undulating configuration provides several features that will be more fully described below, such as an increase in the expansion ratio of the unit cell and of a stent composed of such unit cells with minimal change in the length of the unit cell; a decrease in the occurrence of 'flaring', caused when the unit cell radially expands unevenly as when the looped member extremities do not radially expand as fully as the arm pairs of the unit cell; and a decrease in stress in the expandable looped by a more even distribution of force during placement and expansion.

The expansion of the unit cell and movement of its structural components will now be described with respect to FIG. 3B. FIG. 3B shows the unit cell of FIG. 3A in its expanded, large-diameter condition and like structural elements are identified according to the notation set forth in FIG. 3A. The unit cell is expanded in response to an applied external force, for example, where the unit cell is part of a stent, the stent is mounted on an expanding means, such as a balloon of a balloon catheter, and expanded by inflation of the balloon. In response to the applied force, expansion of the unit cell is achieved by pivotal movement of the arms attached to each end of the elongate bar. The arms pivot at the point of attachment of the inner arm ends to the connecting bar ends and move away from each other in an outward direction. "Outward" as used herein is with respect to the connecting bar, where an outward direction refers to movement away from the connecting bar.

As the arms move outward, the *component length of the* expandable looped member *as measured in an axial direction from an axial outward extremity to an axial inward extremity of the expandable looped member* is caused to [move inward, which as used herein refers to movement toward the connecting bar, and in this case toward the associated end of the connecting bar] *reduce in length in the axial direction. The reduction in the component length of the expandable looped member is approximately equal to the distance the outer arm ends travel in the axial outward direction.* The connecting bar stabilizes the unit cell and provides rigidity for strength. More importantly, the ends of the central bar act as pivot points, allowing for expansion of the unit cell, and at the same time the central bar prevents shortening of the unit cell during expansion.

The unit cell for use in a stent must impart to the stent sufficient flexibility to enable tracking of the stent through often tortuous vascular paths for placement at the treatment site. At the same time, the stent must be strong enough radially to hold open a body lumen.

Figure 4A:
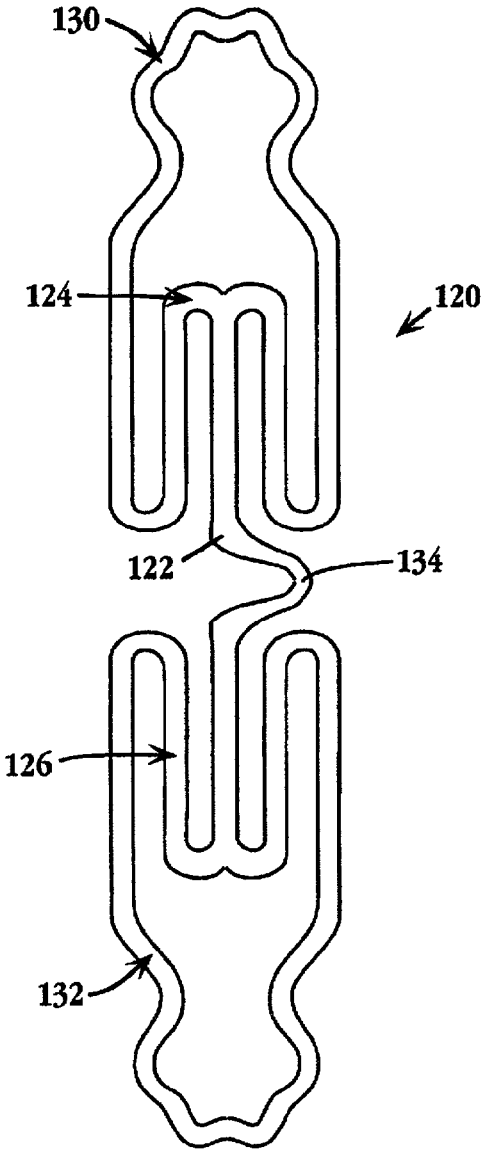
FIGS. 4A-4B are plan views of a unit cell according to other embodiments of the present invention, where the connecting bar is modified to provide increased flexibility.
Figure 4B:
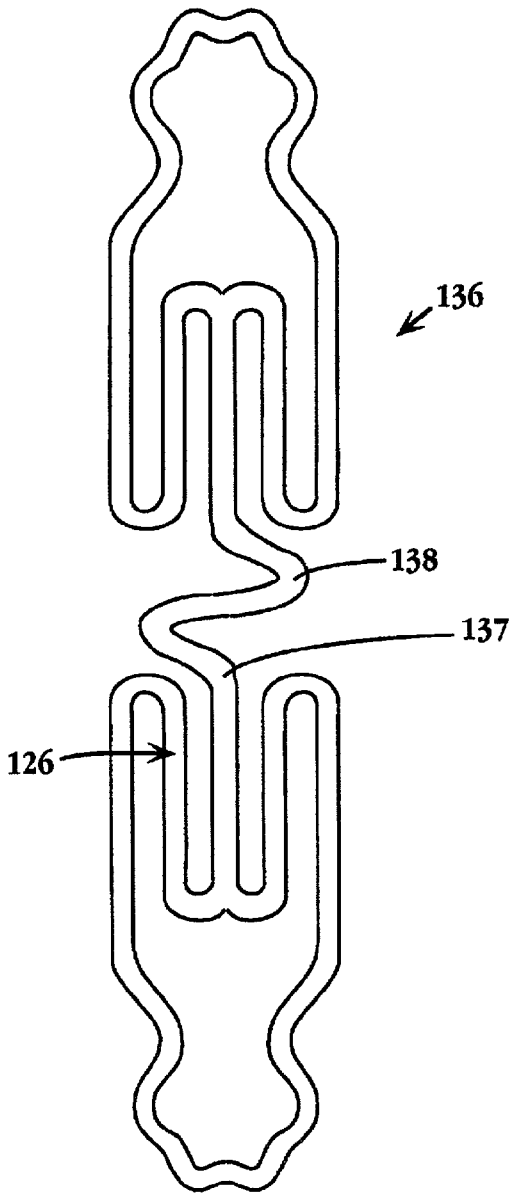

The unit cell of the invention provides a stent having both longitudinal flexibility and radial strength. An important advantage provided by the unit cell of the invention is that the longitudinal flexibility is readily varied through simple modifications of the elements of the unit cell. For example, embodiments of the unit cell having greater flexibility than the embodiment of FIG. 3 are shown in FIGS. 4A-4B. In the embodiment of FIG. 4A, unit cell 120 includes a connecting bar 122 with a pair of arms 124, 126 attached to each end of the connecting bar. The arms in each pair are connected by an expandable looped member, 130, 132. In this embodiment, connecting bar 122 includes a U-shaped loop 134. The loop provides longitudinal flexibility to the unit cell, which lends flexibility to a stent which is formed of a plurality of such unit cells. The unit cell 136 of FIG. 4B includes connecting bar 137 having an S-shaped member 138 for added flexibility.

The flexibility of the unit cell can also be varied by changing the dimensions of the unit cell, e.g., the length and width of the unit cell, the length and width of the unit cell components as well as the relative dimensions. For example, and with reference to FIG. 5A, the length of the unit cell, $l_c$, is varied according to the length a of the connecting bar and the length b of the arms and looped members. Typically, the length of the unit cell $l_c$ is between 1-10 mm, more preferably between 2-8 mm and most preferably between 2-6 mm. Length b is determined primarily by the length of the expandable looped member, where the relative dimension of the axial nose length $b_l$ to length b is variable to vary the flexibility of the unit cell. The flexibility of the unit cell is also varied according to length a of the connecting bar, where a shorter connecting bar results in a more flexible and tractable unit cell. Typical dimensions for a, the length of the connecting bar, are between about 1.5-2.5 mm. Length b is generally between 1.5-4 mm, with b, between 0.50-1.25 mm.

Figure 5A:
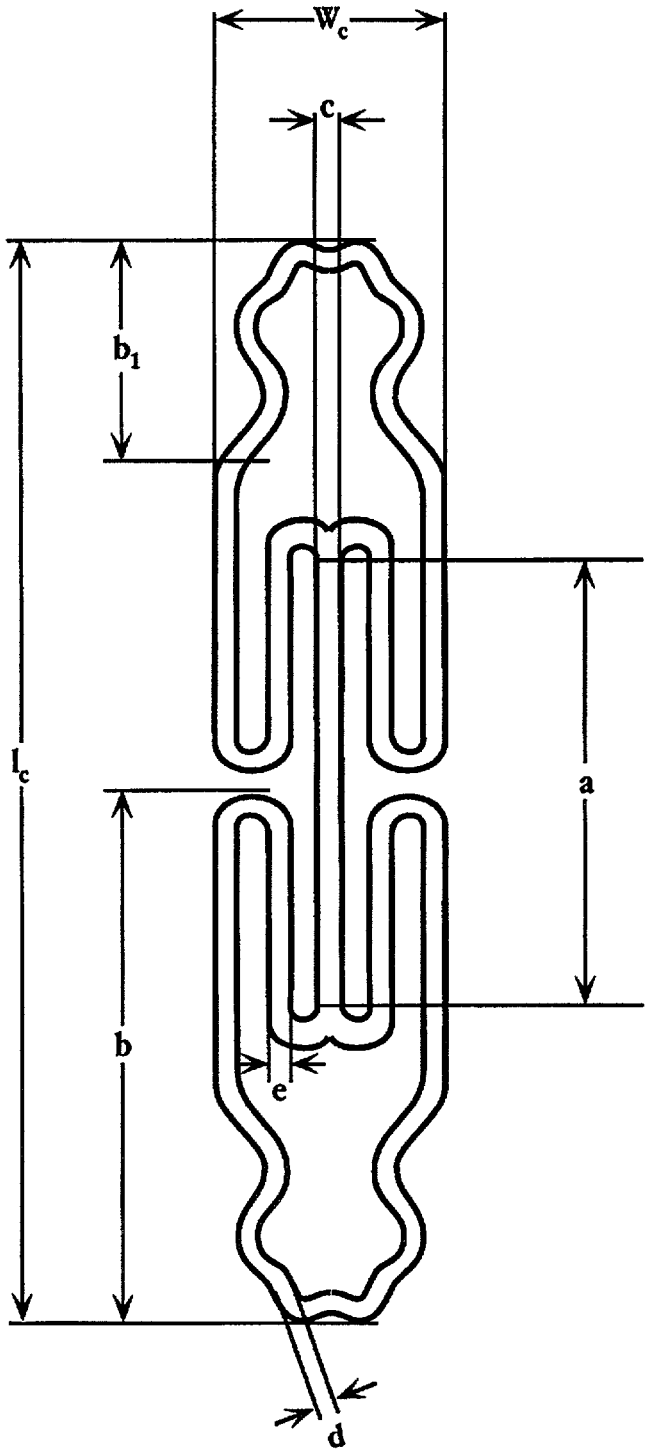
FIGS. 5A-5B are plan views of a unit cell (FIG. 5A) and a plurality of unit cells (FIG. 5B) showing the dimensions of the unit cell and a plurality thereof.

With continuing reference to FIG. 5A, the width $W_c$ of the unit cell is variable according to the material from which the unit cell is made and its dimensions. Typically, the unit cell is prepared from a suitable biocompatible materials such as stainless steel, tungsten, titanium, tantalum, gold, platinum and alloys and combinations of these materials, as well as shape-memory alloys and high strength thermoplastic polymers. The dimensions c and d in FIG. 5A are readily varied according to material and material dimensions. Dimension e corresponds to the dimension of the arm pairs and is variable. Typical dimensions for the overall width of the unit cell, $w_c$, are between 0.40-4.0 mm, with c generally between 0.025-0.13 mm and d between 0.03-0.10 mm and e between 0.04-0.1 mm.

It will be appreciated that dimensions c, d and e can be the same or different within a unit cell. In particular, dimension e is varied to alter the strength and rigidity of the unit cell, particularly when the unit cell is in its expanded condition. It will also be appreciated that the unit cell dimensions, particularly dimensions c and e can vary within a plurality of unit cells and between unit cell pluralities, as will be discussed below.

Figure 5B:
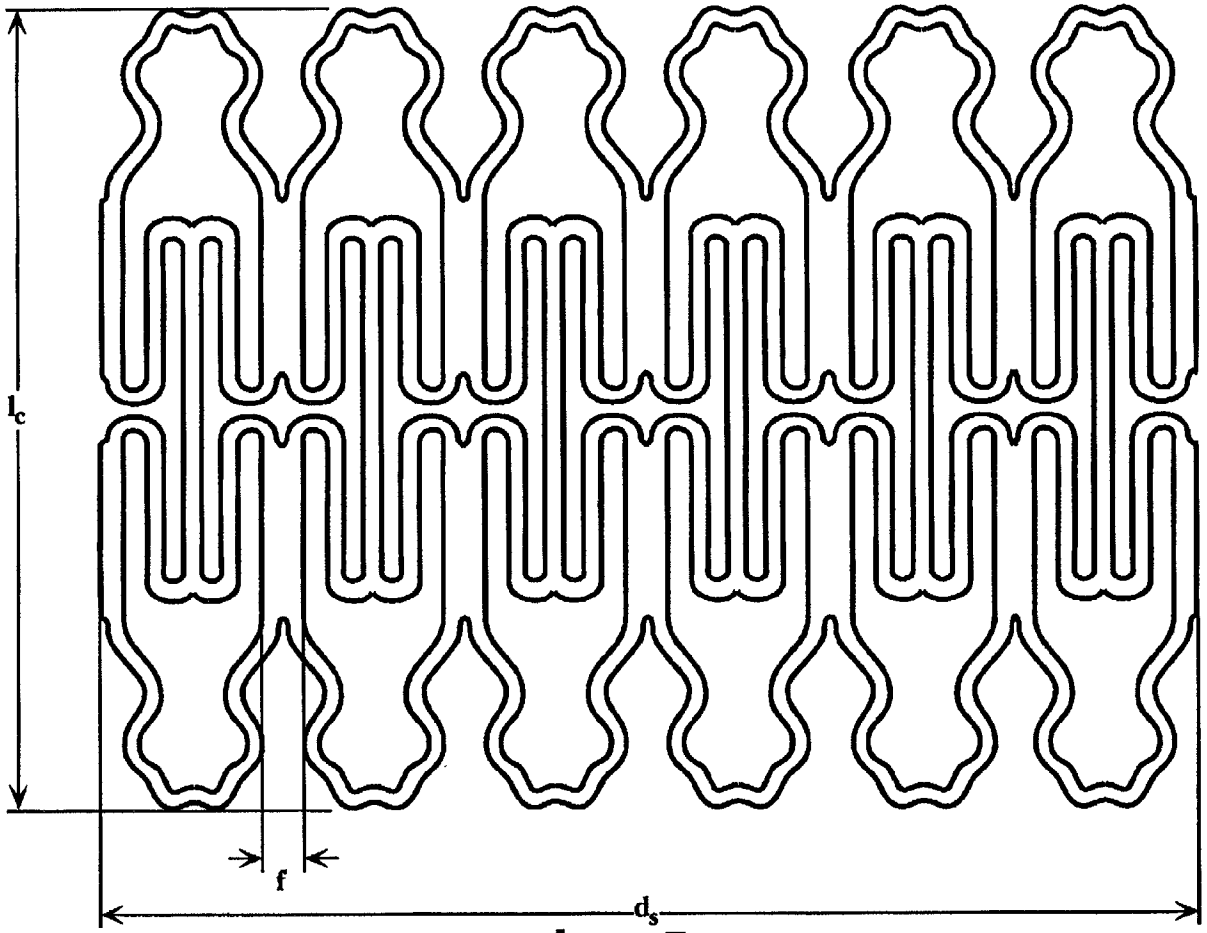

FIG. 5B shows six unit cells joined together to form a plurality, for use in forming a stent in accordance with the invention. The unit cells are joined along adjacent straight portions of looped member extremities, as can be seen in the figure at dimensions It will be appreciated that f is variable according to the dimension of the looped member and the degree to which the adjacent cells are merged or overlapped. The diameter of the stent d, is determined by width of the unit cell and the number n of unit cells so joined. The stent length is determined by the length of the unit cell $l_c$ and the number m of pluralities joined in an axial direction. In this way the stent diameter and length is readily varied to treat vessels of any diameter and lesions of any length.

Figure 6A:
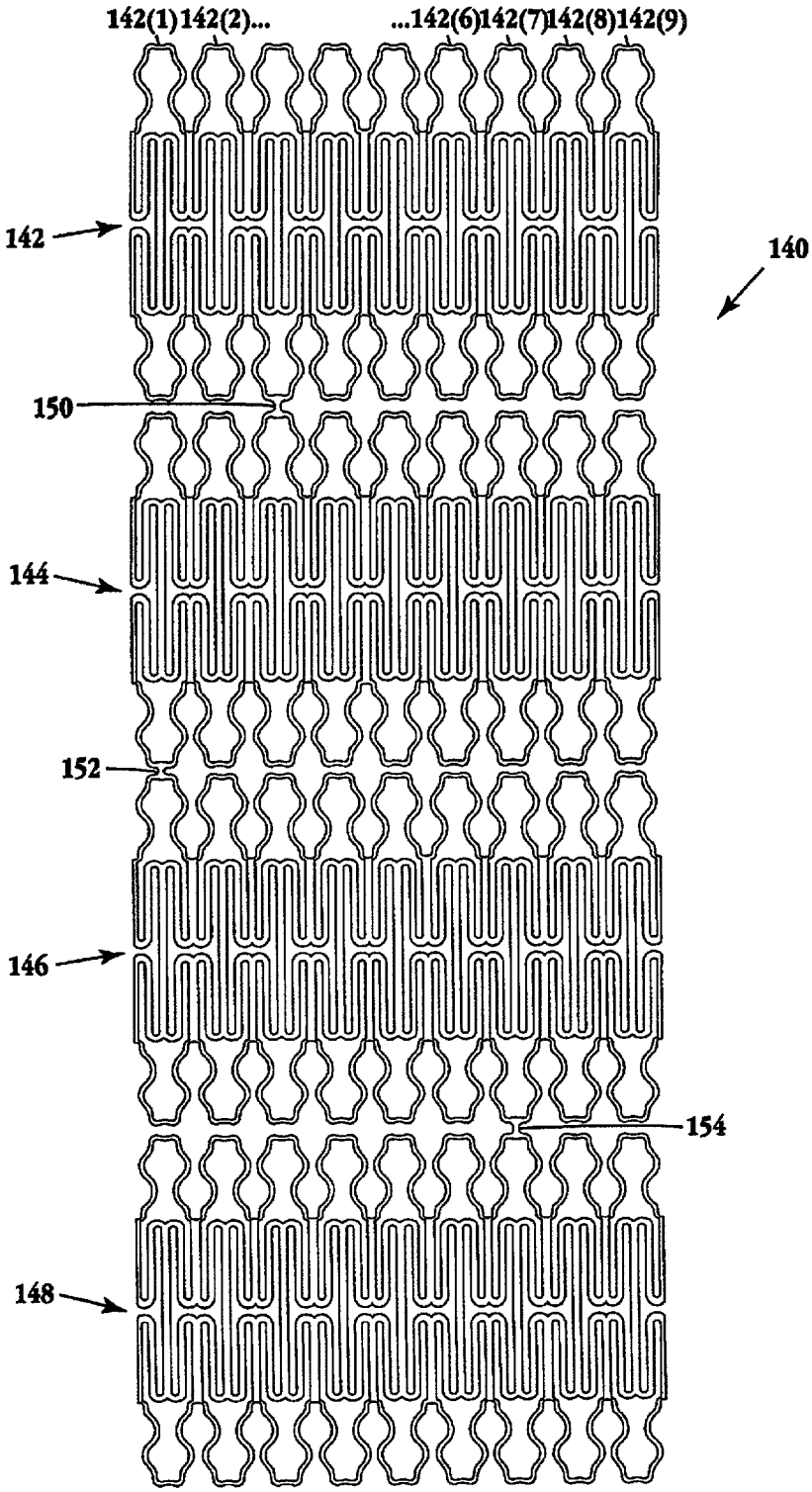
FIGS. 6A-6C are plan views of the stent of the invention which illustrate various embodiments of a connecting segment for axially connecting a plurality of unit cells.
Figure 6B:
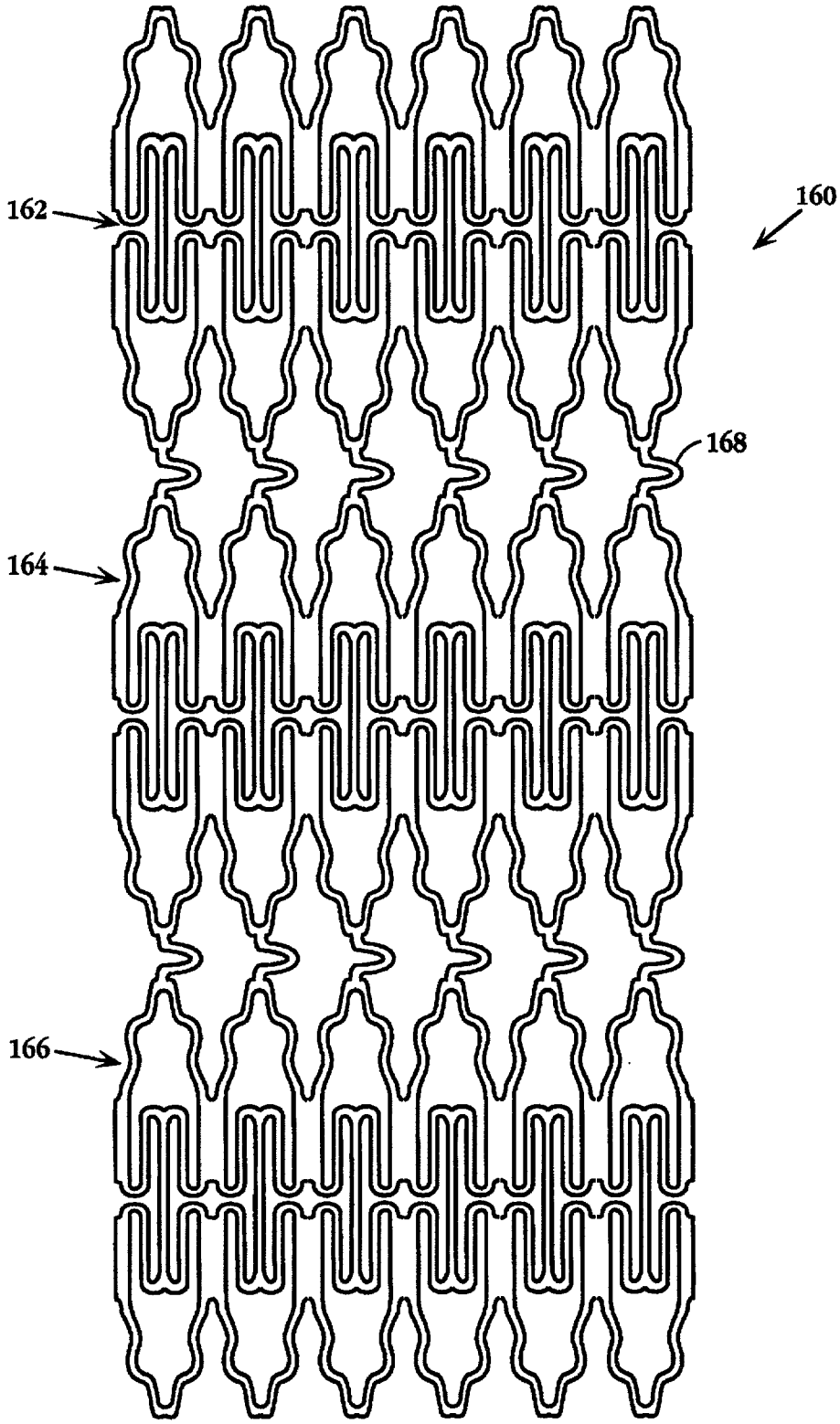
Figure 6C:
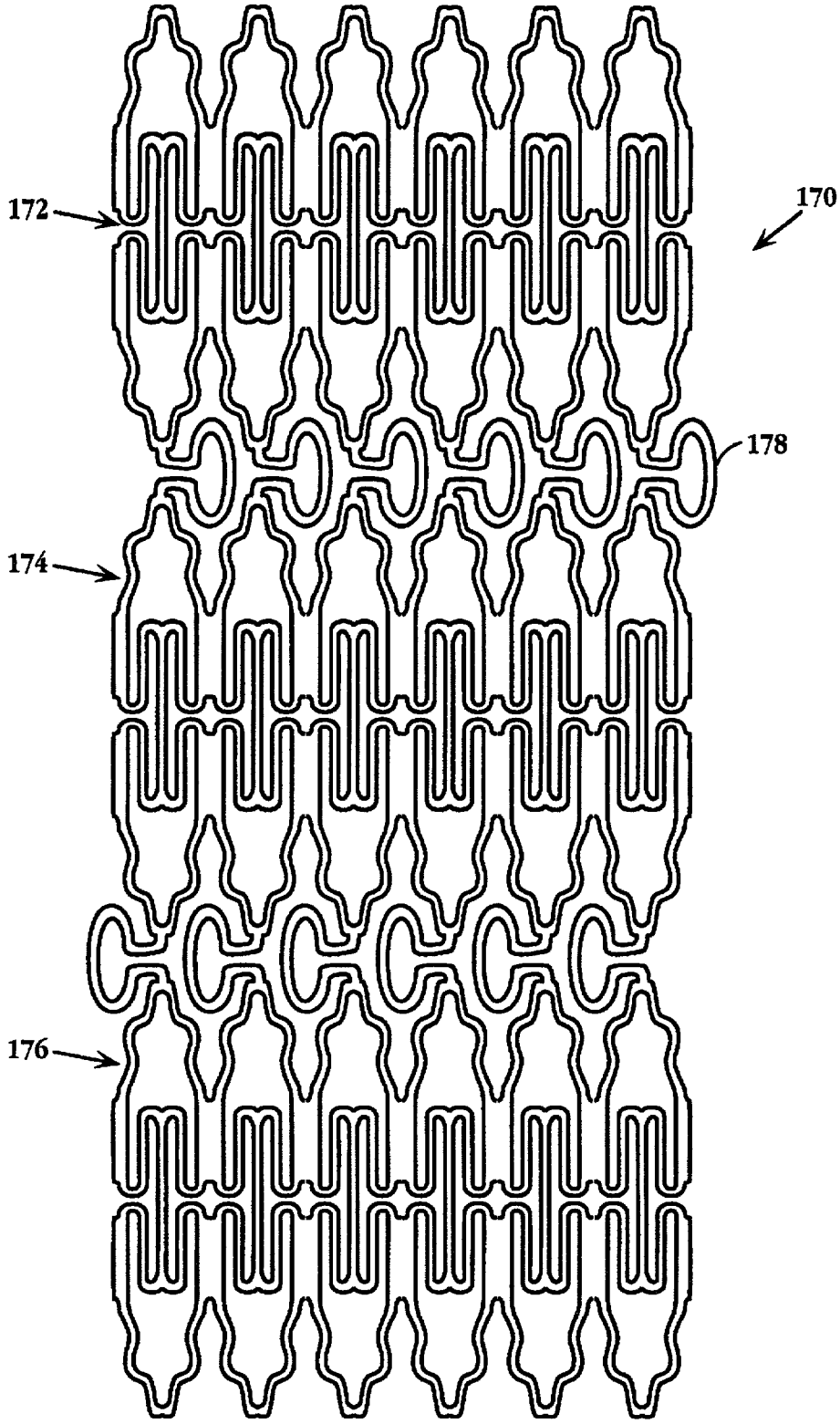

FIGS. 6A-6C are plan views of stents according to the invention composed of unit cells as described above. In FIG. 6A, stent 140 is composed of m pluralities of unit cells, where m in this embodiment is four, e.g., pluralities 142, 144, 146, 148. Each plurality is composed of n unit cells, where n in this embodiment is nine, e.g., unit cells 142(1)-142(9). As discussed above, the unexpanded diameter of the stent is determined by the number n of unit cells in each plurality and the dimensions of the unit cell. The length of the stent is determined by the dimensions of the unit cell and the number m of pluralities.

With continuing reference to FIG. 6A, pluralities 142, 144, 146, 148 are joined to an adjacent plurality by a connecting segment, such as segments 150, 152, 154. The connecting segment most broadly is any means to join one unit cell to another, to connect one plurality of unit cells to another for formation of a stent from the unit cells of the invention. The connecting segment can be of a variety of configurations, as will be illustrated, including a simple weld joint between two unit cells (FIG. 6E) or a distinct segment (FIGS. 6A-6D). The connecting segment can be an integral part of the unit cells with which it is in contact, or it can be formed independently of the same or a different material and secured to the nose portion of the looped extremity of the unit cells. The number and position of the connecting segments joining pluralities can be varied to alter the flexibility of the stent, as can the structure of the connecting segment itself, as will be seen in the embodiments of FIGS. 6B-6E below.

FIGS. 6B-6E show alternative embodiments of the connecting segment. In FIG. 6B, stent 160 is formed of three pluralities of unit cells, 162, 164, 166. The pluralities are joined by connecting segments, such as segment 168, between axially adjacent unit cells. The connecting segments are a U-shaped loop, which provides increased tractability and flexibility to the stent, relative to the embodiment of FIG. 6A.

FIG. 6C shows a stent 170 where pluralities of unit cells 172, 174, 176 are joined by connecting segments having a large loop configuration, such as connecting segment 178. It will be appreciated that in the embodiments of FIGS. 6B-6C the number and position of connecting segments between pluralities is variable.

Figure 6D:
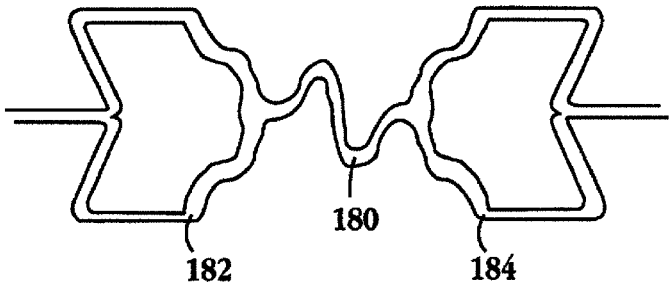
FIGS. 6D-6E shows other embodiments of the connecting segment for joining unit cells and pluralities of unit cells in a stent of the invention.
Figure 6E:
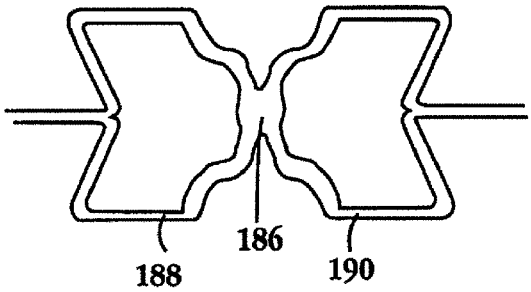

FIGS. 6D-6E illustrate two further embodiment of a connecting segment in accordance with the invention. In these figures, the connecting segment joining the axial extremities of looped members in shown, rather than the entire stent. In the embodiment of FIG. 6D, the connecting segment 180 is an S-shaped member joining looped members 182, 184. In FIG. 6E, the connecting segment 186 is a butt-weld joint between looped extremities 188, 190.

It will be appreciated that different connecting segments can be used in a single stent, to alter the rigidity and tractability of the stent. For example, a more rigid connecting segment such as the weld joint of FIG. 6E can be used to join pluralities at the ends of the stent, for good tractability, and more flexible connecting segments can be used to join inner stent pluralities to maintain flexibility.

One important feature of the stent of the present invention is its capability to expand from a low-profile diameter to a diameter of substantial size while maintaining structural integrity, e.g., radial strength. Also important is that the expansion ratio of the stent, that is, the ratio of the stent's expanded diameter to the stent's unexpanded diameter, is readily varied according to the number of unit cells in the plurality and the dimensions of the unit cell, as is evident from the discussion above. Typically, the number of unit cells in a plurality for use in forming a stent in accordance with the invention is between 3-500, more preferably between 3-150, and most preferably between 3-100. The expansion ratio of the stent can also be varied by changing the axial length of the unit cell. Axial length is taken as the longitudinal or axial distance between the axial extremities in a unit cell and is indicated in FIG. 5A as $l_c$. The longer the axial length, the larger the expansion ratio of the stent, and the more unit cells in each plurality, the larger the expansion ratio.

Stents prepared in support of the present invention have typical expansion ratios of between 1-10. It will be appreciated based on the above description of the stent that for any selected application from the smallest ducts in the body to the largest vessels—the stent of the invention can be tailored through selection of the number and size of unit cells. By way of example, an exemplary stent for use in a vessel of the coronary system, where the vessel has a size of about 2-5 mm, is composed of a plurality of nine unit cells, where each unit cell has an axial length of 3.2 mm. This stent has an expansion ratio of about 5. In addition to vessels in the coronary system, the following vessels are contemplated for use with the stent of the invention: cranial artery (1-3 mm), aorta (2-5 cm), splenic artery (3-6 mm), vena cava (3-5 mm), renal artery (3-5 mm), vessels of the carotid system, such as carotid artery (up to 1.5 cm), internal and external carotid (5 mm), subclavian artery, vertebral artery, brachial artery, iliac vein (1-2 mm), femoral vein or artery, popliteal artery or vein (3-5 mm).

Another important feature of the stent of the present invention is a minimal elastic recoil after expansion to its large-diameter condition. Stents made in support of the invention were mounted on a balloon of a balloon catheter and expanded by inflating the balloon to a pressure between 4-12 atm. The stents had an initial diameter of 1.35 mm and were expanded to between 3.3-3.86 mm, depending on the inflation pressure. After deflation of the balloon, the final expansion diameter of the stent was measured and compared to the expansion diameter measured when the balloon was inflated. Stent of the present invention had a recoil on the order of 1-1.5% (taken as the stent diameter with balloon inflated to the diameter after balloon deflation). The recoil of commercially available stents were determined by the same procedure, and found to have recoils on the order of 3-7%.

The stent of the present invention also provides the advantageous feature of minimal axial shortening upon radial expansion. During the testing procedure described above for recoil, the length of the stent after expansion was measured and compared to the length of the stent prior to expansion. The length of the stents of the present invention decreased by less than 0.5%, typically by about 0.2-0.5% after expansion. In comparison, commercially available stents decreased in length after radial expansion by 3-8%.

The stent described above is preferably constructed of a biocompatible material having good mechanical strength, such as those listed above. It will be appreciated that the radial strength of the stent—that is, its ability to prevent restenosis or to maintain vessel patency, and further to prevent vessel recoil and vessel spasms—is in part a of function of the material from which it is formed and the design and configuration of the stent. Preferred materials for forming the stent include stainless steel, platinum and tantalum and alloys. The stent can be formed from a flat sheet or a tubular structure of material by chemically etching, laser cutting or by electronic discharge machining. A preferred method of making the stent of the invention is by laser cutting, and suitable methods and apparatus are known to those in the art. The stent, after laser cutting or machining can be electropolished, annealed and/or passivated as desired. The stent or a portion of the stent can also be plated or coated with an agent to provide lubricity and/or visibility. For example, the stent can be coated in whole or in part with a radiopaque material or plated with platinum or gold to provide improved visibility during fluoroscopy.

In another embodiment of the invention, the stent described herein is used as a scaffold or structural member for carrying a polymer stent or sheath which preferably contains a therapeutic agent. The polymer stent is preferably carried on the outer surface of the structural stent for coexpansion with the structural stent in response to an applied force. An example of a co-expandable metal/polymer stent is described in U.S. Pat. No. 5,674,242, incorporated herein by reference.

Figure 7A:
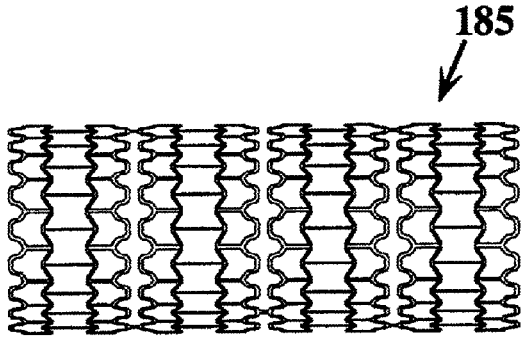
FIGS. 7A-7B show a stent in accordance with the invention (FIG. 7A) with a coaxial polymer member (FIG. 7B)
Figure 7B:
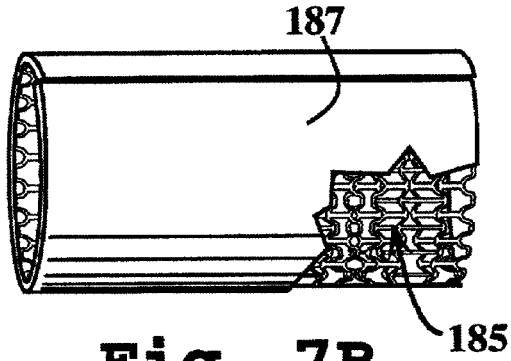

An illustration of such a stent is shown in FIGS. 7A-7B, where a stent 185 as described in FIG. 6A is shown in its expanded condition in FIG. 7A. In FIG. 7B, stent 185 (visible in the cut-away portion) is encased by a polymer member 187.

The stent of the present invention is particularly suited for use as a structural stent because of the uniform nature of the reticulated structure of the stent in its open, expanded condition. A polymer member carried about the outer periphery of the expanded structural stent is sufficiently supported to prevent the polymer from 'sagging' and potentially obstructing the lumen. The stent of the invention can be tailored for the embodiment, by forming notches or depressions in the structure where the coextensive polymer stent is in contact. In this way, the profile of the polymer/metal stent is not increased.

FIGS. 8A-8D illustrate introduction, expansion and deployment of the stent of the invention in a body lumen. It will be appreciated that the stent of the invention is suitable for use in a variety of applications, including, but not limited to, prevention of restenosis, reinforcement of reopened, previously obstructed bile ducts and support of narrowing lumens, such as the esophagus, intestine or urethra.

Figure 8A:
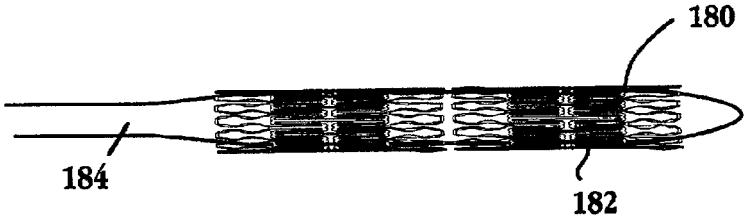
FIGS. 8A-8D illustrate introduction, expansion and deployment of the stent of the invention in a vessel.

With continuing reference to FIGS. 8A-8D, and initially with particular reference to FIG. 8A, a stent 180 is mounted on a balloon portion 182 of a catheter 184. The stent is secured on the catheter by simply compressing it in place for a snug fit over the balloon. Other means to secure the stent to the balloon include temporary adhesives or a withdrawable sleeve, or through ridges or collars on the balloon to restrain lateral movement of the stent.

Figure 8B:
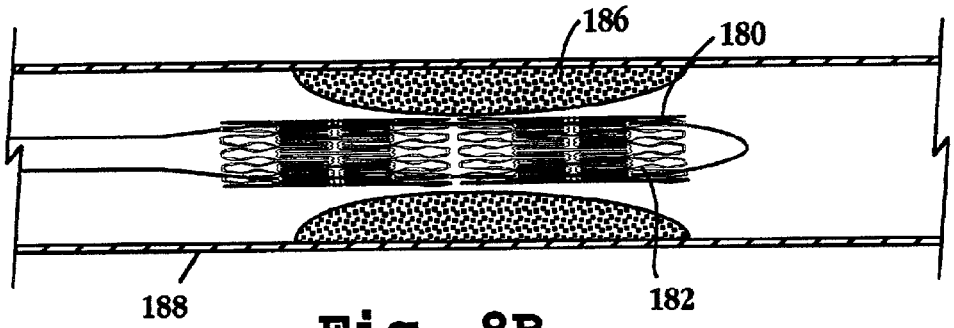
Figure 8C:
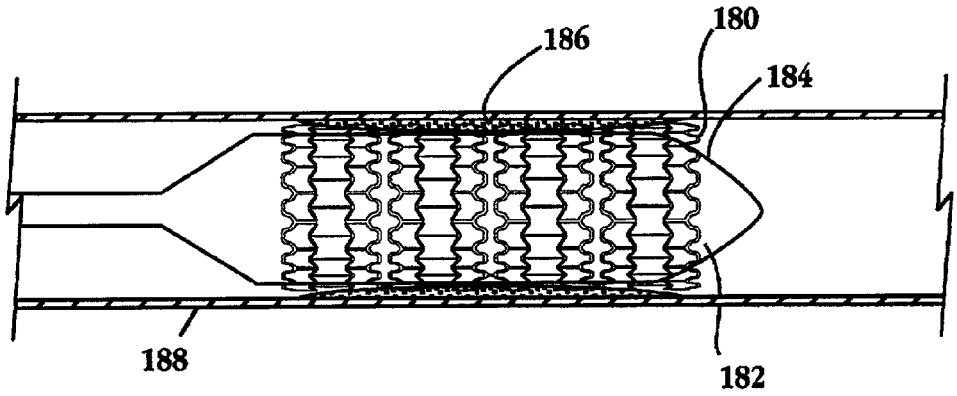

The catheter-stent assembly of FIG. 8A is then advanced through a body lumen of a patient to a treatment site, as shown in FIG. 8B. Once balloon 182 is positioned at the site it is to be implanted, typically across a lesion such as a plaque deposit 186 within a vessel 188, the balloon portion of the catheter is inflated by known means, as depicted in FIG. 8C. The inflation of the balloon causes expansion of the stent from its small-diameter, unexpanded condition of FIG. 8A to its larger-diameter, expanded condition. The stent radially expands and presses against the lesion, contacting the vessel wall and exerting a radial pressure on the vessel wall.

Figure 8D:
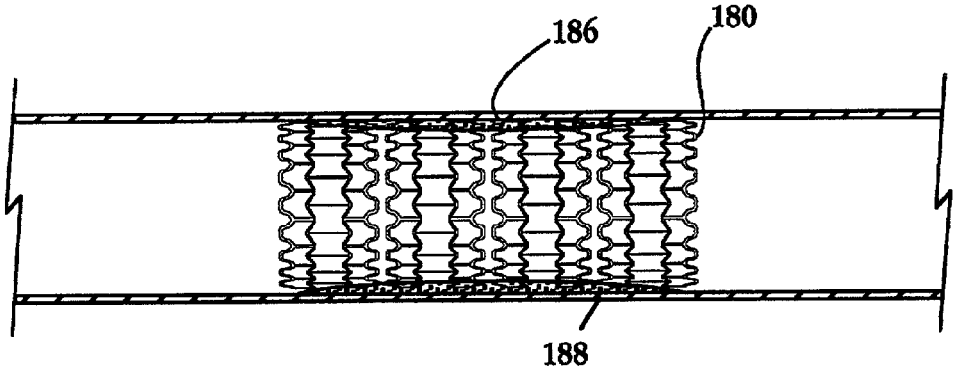

The balloon is then deflated and the catheter is removed from the vessel. The stent remains in its expanded form within the vessel, as shown in FIG. 8D, to prevent reclosure or obstruction of the vessel.

From the foregoing, it can be appreciated how various features and objects of the invention are met. The basic unit cell of the invention provides a structure which radially expands with minimal axial shortening. The expansion ratio of the unit cell is readily varied through selection of the dimensions of the unit cell components. Any number of unit cells can be joined radially and axially to form an expandable structure, such as a stent for insertion into a body lumen. It will of course be appreciated that the unit cell will have application in other types of medical device or in other fields which use a radially expandable member.

Although the invention has been described with respect to particular embodiments, it will be apparent to those skilled in the art that various changes and modifications can be made without departing from the invention.

We claim:

1. A unit cell for use in a stent adapted to be expanded to conform to the dimensions of a vessel, comprising;

(i) an elongate connecting bar extending in a direction normal to the direction of stent expansion, (ii) associated with each end of said connecting bar, a *pair of arms including a* first arm and a second arm, each arm being attached to the connecting bar associated end at an inner arm end for pivotal movement away from one another with stent expansion, said first and second arms having outer arm ends which are moved outwardly, with respect to the connecting bar, with such pivotal movement, and (iii) an expandable looped member connecting the outer arm ends in each pair of first and second arms, said looped member having an axial [extremity which moves axially inwardly, with respect to the associated connecting bar end.] *component length as measured in an axial direction from an axial outward extremity to an axial inward extremity, wherein the axial component length reduces* with stent expansion, said arms and expandable looped members being constructed and dimensioned so that the [radial] *axial* outward distance traveled by the arms' outer ends in each pair of first and second arms is approximately equal to the [axial inward distance traveled by] *reduction in length of the axial component length of* the associated looped member [extremity,] as the stent is expanded.

2. The unit cell of claim 1, wherein said first and second arms in each pair are connected to said looped members through a shoulder member.

3. The unit cell of claim 2, wherein said shoulder member is a U-shaped, N-shaped or W-shaped shoulder member.

4. The unit cell of claim 1, wherein said looped members have an undulating configuration.

5. A stent adapted to be expanded to conform to the dimensions of a vessel, comprising a plurality of unit cells, each unit cell composed of (i) an elongate connecting bar extending in a direction normal to the direction of stent expansion, (ii) associated with each end of said connecting bar, a first arm and a second arm, each arm being attached to the associated connecting bar end at an inner arm, for pivotal movement away from one another with stent expansion, said first and second arms having outer arm ends which are moved outwardly, with respect to the connecting bar, with such pivotal movement, and (iii) an expandable looped member connecting the outer arm ends in each pair of first and second arms, said looped member having an axial [extremity which moves axially inwardly, with respect to the associated connecting bar end,] *component length as measured in an axial direction from an axial outward extremity to an axial inward extremity, wherein the axial component length reduces* with stent expansion, said arms and expandable looped members being constructed and dimensioned so that the axial outward distance traveled by the arms' outer ends in each pair of first and second arms is approximately equal to the [axial inward distance traveled by] *reduction in length of the axial component length of* the associated looped member [extremity,] as the stent is expanded.

6. The stent of claim 5, wherein said first and second arms in each pair are connected to said looped members through a shoulder member.

7. The stent of claim 6, wherein said shoulder member is a U-shaped, N-shaped or W-shaped shoulder member.

8. The stent of claim 5, wherein said axial extremity in each of said looped members has an undulating configuration.

9. The stent of claim 5, wherein said plurality of unit cells is connected to one or more axially adjacent plurality of unit cells by at least one connecting segment extending between two axially adjacent axial extremities.

10. The stent of claim 9, wherein each plurality of unit cells includes between 3-500 unit cells.

11. The stent of claim 9, wherein the stent has an expansion ratio, taken as the diameter of the stent after expansion to the diameter before expansion, of between 1-10.

12. The stem of claim 11, wherein the expansion ratio is varied by varying the axial length, taken as the distance between axial extremities in a unit cell, of the unit cells in each plurality of unit cells.

13. The stent of claim 11, wherein the expansion ratio is varied by varying the number of unit cells in each plurality.

14. The stent of claim 9, wherein said connecting segment is a U-shaped looped segment.

15. The stent of claim 5, which further includes an outer stent surface on which a polymer stent is carried, said stent and polymer stent designed for coexpansion in response to an applied force.

*16. A stent having a plurality of openings therethrough, the stent comprising a plurality of serpentine circumferential bands, adjacent serpentine circumferential bands connected one to the other, the serpentine circumferential bands including first serpentine circumferential bands of a first shape and second serpentine circumferential bands of a second shape different from the first shape, every first serpentine circumferential band being adjacent to a said second serpentine circumferential band and every second serpentine circumferential band being adjacent to a said first serpentine circumferential band, distal most openings of the stent being at least partially bounded by a said first serpentine circumferential band and at least partially bounded by a said second serpentine circumferential band, proximal most openings of the stent being at least partially bounded by a said first serpentine circumferential band and at least partially bounded by a said second serpentine circumferential band, at least one opening not bounded by a said second serpentine circumferential band.*

*17. The stent of claim 16 wherein adjacent first and second serpentine circumferential bands are connected one to the other via a plurality of longitudinally extending connectors.*

*18. The stent of claim 17 wherein a said first serpentine circumferential band has a width which differs from the width of a said second serpentine circumferential band.*

*19. The stent of claim 17 wherein the serpentine circumferential bands comprise alternating peaks and troughs, the adjacent first and second serpentine circumferential bands being connected only via the longitudinal connectors, a portion of the longitudinal connectors extending between peaks of the first and second serpentine circumferential bands, a portion of the longitudinal connectors extending between troughs of the first and second serpentine circumferential bands.*

*20. The stent of claim 16 wherein a said first serpentine circumferential band has a width which differs from the width of a said second serpentine circumferential band.*

*21. The stent of claim 16 wherein adjacent serpentine circumferential bands are connected one to the other via one or more longitudinally extending connectors.*

*22. A stent having a plurality of openings therethrough, the stent comprising a plurality of serpentine circumferential bands, adjacent serpentine circumferential bands connected one to the other, the serpentine circumferential bands including first serpentine circumferential bands of a first shape and second serpentine circumferential bands of a second shape different from the first shape, every first serpentine circumferential band being adjacent to a said second serpentine circumferential band and every second serpentine circumferential band being adjacent to a said first serpentine circumferential band, at least one said first serpentine circumferential band adjacent to and connected to another said first serpentine circumferential band, distal most openings of the stent being at least partially bounded by a said first serpentine circumferential band and at least partially bounded by a said second serpentine circumferential band, proximal most openings of the stent being at least partially bounded by a said first serpentine circumferential band and at least partially bounded by a said second serpentine circumferential band, wherein adjacent first and second serpentine circumferential bands are connected one to the other via a plurality of longitudinally extending connectors, wherein a said first serpentine circumferential band has a width which differs from the width of a said second serpentine circumferential band,*

*wherein the serpentine circumferential bands comprise alternating peaks and troughs, the adjacent first and second serpentine circumferential bands being connected only via the longitudinal connectors, a portion of the longitudinal connectors extending between peaks of the first and second serpentine circumferential bands, a portion of the longitudinal connectors extending between troughs of the first and second serpentine circumferential bands.*

*23. A stent having a plurality of openings therethrough, the stent comprising a plurality of serpentine circumferential bands, adjacent serpentine circumferential bands connected one to the other, the serpentine circumferential bands including first serpentine circumferential bands of a first shape and second serpentine circumferential bands of a second shape different from the first shape, every first serpentine circumferential band being adjacent to a said second serpentine circumferential band and every second serpentine circumferential band being adjacent to a said first serpentine circumferential band, at least one said first serpentine circumferential band adjacent to and connected to another said*

*first serpentine circumferential band, distal most openings of the stent being at least partially bounded by a said first serpentine circumferential band and at least partially bounded by a said second serpentine circumferential band, proximal most openings of the stent being at least partially bounded by a said first serpentine circumferential band and at least partially bounded by a said second serpentine circumferential band, wherein adjacent serpentine circumferential bands are connected one to the other via one or more longitudinally extending connectors,*

*the longitudinally extending connectors comprising first longitudinal connectors of a first length and second longitudinal connectors of a second length less than the first length.*

*24. The stent of claim 23 wherein the serpentine circumferential bands comprise alternating peaks and troughs, the first longitudinal connectors extending between peaks of some adjacent serpentine circumferential bands and between troughs of other adjacent serpentine circumferential bands, the second longitudinal connectors extending between peaks and troughs.*

*25. A stent comprising a plurality of sections, each section comprising a plurality of loop members, the loop members arranged to form first bands extending about the circumference of the stent, each first band comprising alternating peaks and troughs, each peak separated from a trough adjacent thereto and connected thereto by a bent portion of a loop member, first bands which are adjacent one another within a section separated one from the other by a second band, each second band connected to each first band adjacent thereto, said second bands shaped differently from said first bands, a distal most first band of one section adjacent to and connected to a proximal most first band of another section by a longitudinally extending connecting segment, the longitudinally extending connecting segment connected at a first end to a distal portion of the distal most first band and connected at a second end to a proximal portion of the proximal most first band, wherein a first band of a section is located at an end of the stent.*

*26. The stent of claim 25 wherein first and second bands which are adjacent one another are connected one to the other via longitudinally extending connectors.*

*27. The stent of claim 26 wherein each second band is in the form of two adjacent, out of phase, interconnected serpentine structures.*

*28. A stent comprising a plurality of circumferential serpentine bands including first circumferential serpentine bands and second circumferential serpentine bands, the first circumferential serpentine bands having a width in excess of the width of the second circumferential serpentine bands, circumferential serpentine bands which are adjacent one another connected one to the other, at least one second serpentine circumferential band immediately adjacent to and connected to another second serpentine circumferential band by a straight longitudinal connector.*

*29. The stent of claim 28 wherein adjacent circumferential serpentine bands are connected one to the other via one or more longitudinal connectors.*

*30. The stent of claim 29 wherein the first circumferential serpentine bands have an amplitude in excess of the amplitude of the second serpentine bands.*

*31. The stent of claim 30 wherein each first circumferential serpentine band is adjacent a second circumferential serpentine band and each second circumferential serpentine band is adjacent a first circumferential serpentine band.*

*32. The stent of claim 28 wherein each first circumferential serpentine band is adjacent a second circumferential serpentine band and each second circumferential serpentine band is adjacent a first circumferential serpentine band.*

*33. The stent of claim 28 wherein the first circumferential serpentine bands have an amplitude in excess of the amplitude of the second serpentine bands.*

* * * * *